(12) United States Patent
Pane et al.

(10) Patent No.: US 6,741,084 B2
(45) Date of Patent: May 25, 2004

(54) DEVICE FOR MEASURING THE OXIDIZABLE CARBON OF A LIQUID AND A METHOD FOR THE USE THEREOF

(75) Inventors: David Allen Pane, Lyons, CO (US); John R. Stillian, Longmount, CO (US); Nick R. Jancewicz, Boulder, CO (US); Gastón de Los Reyes, Boston, MA (US); Wisam Yacteen, Waltham, MA (US)

(73) Assignee: Millipore Corporation, Billerica, MA (US)

( * ) Notice: Subject to any disclaimer, the term of this patent is extended or adjusted under 35 U.S.C. 154(b) by 180 days.

(21) Appl. No.: 10/010,542

(22) Filed: Oct. 26, 2001

(65) Prior Publication Data

US 2002/0125898 A1 Sep. 12, 2002

Related U.S. Application Data

(60) Provisional application No. 60/243,599, filed on Oct. 26, 2000.

(51) Int. Cl.[7] .......................... G01R 27/08; G01N 33/00
(52) U.S. Cl. ...................................... 324/693; 436/146
(58) Field of Search .......................... 436/146; 324/693, 324/439, 446, 694, 696; 422/82.02

(56) References Cited

U.S. PATENT DOCUMENTS

| | | | |
|---|---|---|---|
| 4,626,413 A | 12/1986 | Blades et al. | 422/78 |
| 4,666,860 A | 5/1987 | Blades et al. | 436/146 |
| 4,683,435 A | 7/1987 | Blades | 324/442 |
| 4,868,127 A | 9/1989 | Blades et al. | 436/146 |
| 5,046,212 A | 9/1991 | Blades et al. | 422/82.02 |
| 5,260,663 A | 11/1993 | Blades | 324/442 |
| 5,275,957 A | 1/1994 | Blades et al. | 436/133 |
| 5,334,940 A | 8/1994 | Blades | 324/442 |
| 5,395,522 A | 3/1995 | Melanson et al. | 210/202 |
| 5,518,608 A | 5/1996 | Chubachi | 210/96.1 |
| 5,581,189 A | 12/1996 | Brenn | 324/439 |
| 5,677,190 A | 10/1997 | Melanson et al. | 436/141 |

FOREIGN PATENT DOCUMENTS

| | | | |
|---|---|---|---|
| EP | 0498888 | 8/1992 | G01N/27/06 |

OTHER PUBLICATIONS

International Search Report for PCT/US01/46628 (Forms PCT/ISA/220 and 210), mailed Nov. 6, 2002.

*Primary Examiner*—N. Le
*Assistant Examiner*—Amy He
(74) *Attorney, Agent, or Firm*—John Dana Hubbard

(57) ABSTRACT

The present invention provides a device useful in the photo-oxidation of a sample liquid and in the measurement of the oxidized carbon content thereof. The device includes a cell, at least two elongate probes, and a temperature sensitive element. The cell includes a rigid light-transmissive outer wall that encloses a continuous predetermined internal volume The elongate probes—providing collectively the ability to measure temperature and conductivity—penetrate through the rigid outer wall and extend substantially into the cell's internal volume. At least one of the elongate probes is hollow at least partially along its length, the temperature sensitive element being positioned within this bore. A methodology involving the use of the device is also described.

10 Claims, 1 Drawing Sheet

DEVICE FOR MEASURING THE OXIDIZABLE CARBON OF A LIQUID AND A METHOD FOR THE USE THEREOF

REFERENCE TO RELATED APPLICATION

This application claims the benefit of Provisional U.S. Pat. App. Ser. No. 60/243,599, filed Oct. 26, 2000.

FIELD

The present invention relates in general to a device for measuring the oxidizable carbon of a liquid, and more particularly, to a device for determining the oxidizable carbon content of a liquid by obtaining an accurate thermally-corrected conductivity measurement of a photo-oxidized sample of said liquid.

BACKGROUND

Instruments (and methods) for photo-oxidizing water and measuring the total oxidizable carbon (TOC) content thereof are well-known. Such devices operate primarily by exposing a sample of water, presumably containing dissolved organic constituents, to ultraviolet radiation ("UV"), while contemporaneously measuring the change in electrical conductivity of the sample due to the formation of carbon dioxide by oxidation of said organic constituents. See e.g., U.S. Pat. No. 4,626,413, issued to F. K. Blades et al. on Dec. 2, 1996; 4,666,860, issued to F. K. Blades et al. on May 19, 1987; and U.S. Pat. No. 5,047,212, issued to F. K. Blades et al. on Sep. 10, 1991. Circuits employed in such instruments are disclosed in U.S. Pat. No. 4,683,435, issued to F. K. Blades on Jul. 28, 1987; U.S. Pat. No. 5,334,940, issued to F. K. Blades on Aug. 2, 1994; and U.S. Pat. No. 5,260,663, issued to F. K. Blades on Nov. 9, 1993.

As typically implemented in the cited patents, the instruments for measuring the total oxidizable carbon content of water disclosed in the cited patents comprise a sample cell wherein a static sample of water is maintained between a pair of conductivity-measuring electrodes while the sample and the electrodes are exposed to an irradiation source emitting UV light in the 184 and 253 nanometer wavelengths. The electrodes are typically formed of solid titanium oxidized to provide a $TiO_2$ surface; this N-type semiconductor material catalyzes the reaction of organic carbon compounds in water to $CO_2$ when exposed to short wavelength UV.

Operation of these instruments is subject to some uncertainty. Conductivity—the variable such instruments most immediately target—fluctuates as a function of the temperature of the sample. This is a concern. The standard temperature at which conductivity values are typically reported is 25° C. However, the sample liquid temperature is hardly ever exactly at 25° C. when measured.

To account for such temperature effect, many basic conductivity measuring instruments attach or incorporate a thermal sensor to or into their outer cell walls. From such "extracellular" location, temperature readings are taken and imputed to represent the temperature within and throughout the cell's internal volume. The variance from 25° C. is then calculated into the measured conductivity to correct for any temperature-effect. Examples of such prior art instruments can be found in the patent literature.

For example, U.S. Pat. No. 5,047,212, issued to F. K. Blades et al. on Sep. 10, 1991, discloses a disk-shaped conductivity measuring instrument comprising a circular inner electrode and a concentric outer electrode. The circular inner electrode forms one face of the instrument's internal enclosed volume, with the concentric outer electrode seated therein. A ring-shaped photo-oxidation source is incorporated into the instrument, proximate to the enclosed internal volume. A thermistor is integrated into the inner electrode and is used to measure the water temperature in the cell. In early derivatives of this technology, the inner electrodes tended to be comparatively bulky, and accordingly, had comparatively high thermal mass. Later derivatives—see e.g., the Access 643 TOC Analyzer available from the Anatel Corporation of Boulder, Colo.—offered cells with significantly reduced mass (e.g., circa 1.73 g).

As another example, U.S. Pat. No. 5,677,190, issued to P. C. Melanson et al. on Oct. 14, 1997, discloses "[a]n improved measurement cell . . . for measuring the electrical characteristics of a liquid sample during exposure to radiation." More particularly, a glass cell forms a main tube extending generally parallel to an elongated photo-irradiation source. A pair of electrodes are disposed axially within the sample tube. Inlet and outlet tubes and a "temperature sensing well" are fused to the main tube.

Although these and other prior art conductivity measuring instruments continue to be useful, in respect of capturing very fine conductivity measurements, certain observations can be noted regarding their precision in the measurement of temperature.

First, in many prior art instruments, temperatures sensors are often secured to the housing of the cell, isolated from the liquid loaded within the cell reducing or otherwise frustrating thermal accuracy.

Second, the conduct of photo-oxidation on a sample liquid will in time produce thermal gradients within that sample. Thus, for example, the temperature of the sample liquid closest to the irradiation source will be higher than the temperature of the sample liquid furthest from the source. This can reduce the precision and/or accuracy of prior art instruments wherein the temperature sensor is remote from the electrodes. Such sensors will not measure the temperature in the area wherein conductivity is measured. Though one may wait for the photo-oxidized sample to equilibrate, this is often impractical.

Third, in prior art devices wherein the thermal sensor is embedded into a bulky electrode, the comparatively high thermal mass of such electrode will frustrate precise and/or accurate thermal readings. Depending on the materials used for such electrode, the temperature sensor may in operation be measuring the temperature of the electrode, rather than the sample liquid. This issue becomes compounded in instruments wherein the sensor is located within its own housing, surrounded by a variety of cell components, each such component having its own thermal mass and thermal conductivity relative to the liquid.

Fourth, in prior art instruments wherein the temperature sensor is located adjacent the outer wall of the cell, unmitigated thermal conduction through exterior walls can lead to an inaccurate temperature measurement. Depending on the materials used for the construction thereof, an instrument's cell wall can conduct the temperature of the external ambient environment to the sample liquid in the vicinity of said cell wall.

In light of the above, there is a need for a new probe and cell design for use in a photo-oxidation based conductivity measuring device, which improves upon the present probes and cells currently used therein in respect of providing more precise temperature readings.

SUMMARY

In consideration of the above need, the present invention provides a device capable of making an improved determination of the oxidizable carbon content of a liquid by obtaining a precise thermally-corrected conductivity measurement of a photo-oxidized sample of said liquid. The conductivity measurement is—as is the case in other prior art device—thermally-corrected, but is particularly characterized by its unprecedented precision in the face of thermal gradients often produced during photo-oxidation. This precision is accomplished, in part, by the unprecedented incorporation into the device of certain materials and structures that permit the taking of "intracellular" thermal measurements (i.e., thermal measurements deep within the device's internal volume) without undesirably compromising other important cell functions.

In one principal embodiment, the device comprises a cell, at least two elongate probes, and a temperature sensitive element (e.g., a thermistor). The cell comprises a rigid light-transmissive outer wall enclosing a continuous predetermined internal volume The elongate probes—which provide collectively the means to measure temperature and conductivity—penetrate through the rigid outer wall and extend substantially into the cell's internal volume. At least one of the elongate probes is hollow at least partially along its length, with the temperature sensitive element positioned well within the resultant bore.

Two principal configurations are envisaged. In the first, two elongate probes are utilized, the pair functioning as electrodes for the measurement of conductivity, with one being hollow for the placement of the temperature sensitive element. In the second, the temperature sensitive element is placed in a hollow elongate probe positioned between paired elongate electrode probes.

In light of the above, it is a principal object of the present invention to provide an improved device capable of being used for photo-oxidizing a liquid and for obtaining a precise thermally-corrected measurement of the total oxidizable carbon (TOC) content thereof.

It is another object of the present invention to provide a methodology for determining the total oxidizable carbon (TOC) content of a liquid, the methodology involving a combination of both photo-oxidation steps and steps designed to reduce the effects of thermal gradients induced thereby.

Other objects will be apparent from the detailed description below and would include, for example, the provision of:

a conductivity probe having an improved thermal reading capability and greater sensitivity in conductivity readings especially at low conductivity levels;

a conductivity probe containing a thermal sensor having a thermal reading capability of +/−1.0% as compared to the temperature of the liquid as measured by a salt thermometer test;

a conductivity probe containing a thermal sensor having a thermal reading capability of +/−0.75% as compared to the temperature of the liquid as measured by a salt thermometer test;

a conductivity cell having a low cell constant and a conductivity probe having an improved thermal reading capability;

a conductivity cell having a cell constant less than approximately 1 $cm^{-1}$;

a conductivity cell having a cell constant between approximately 0.05 to approximately 1 $cm^{-1}$; and a conductivity cell having a cell constant between proximately 0.1 and approximately 1 $cm^{-1}$ and capable of taking precise thermal measurements.

For further understanding of the nature and objects of the present invention, reference should be had to the following description considered in conjunction with the accompanying drawings.

Figure 1:
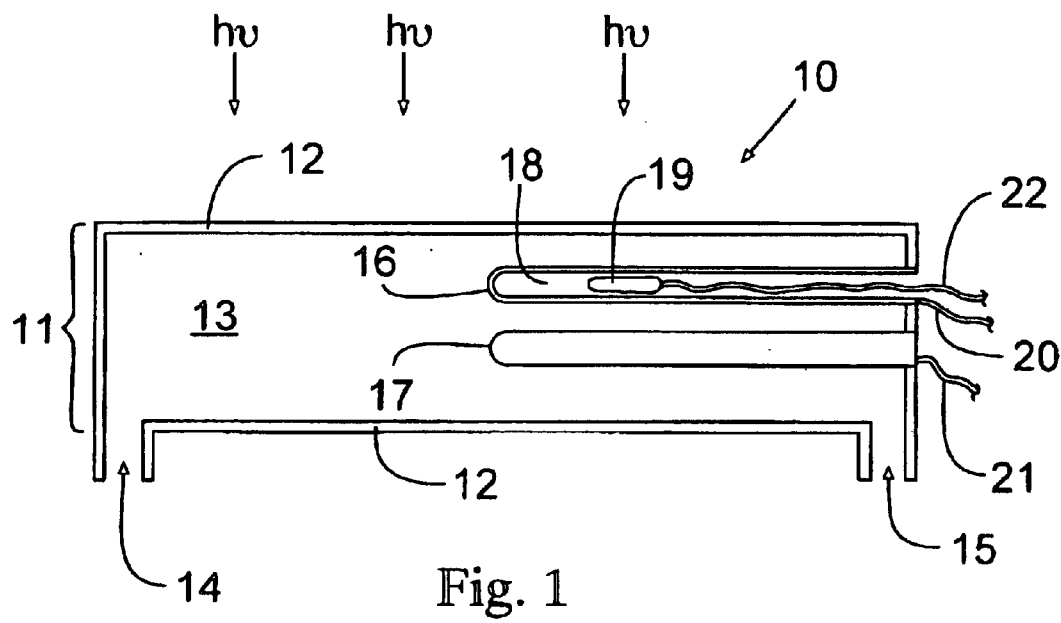
FIG. 1 is a cross-sectional view of a device 10 for measuring the organic content of a photo-oxidized sample liquid according to one embodiment of the present invention.
Figure 2:
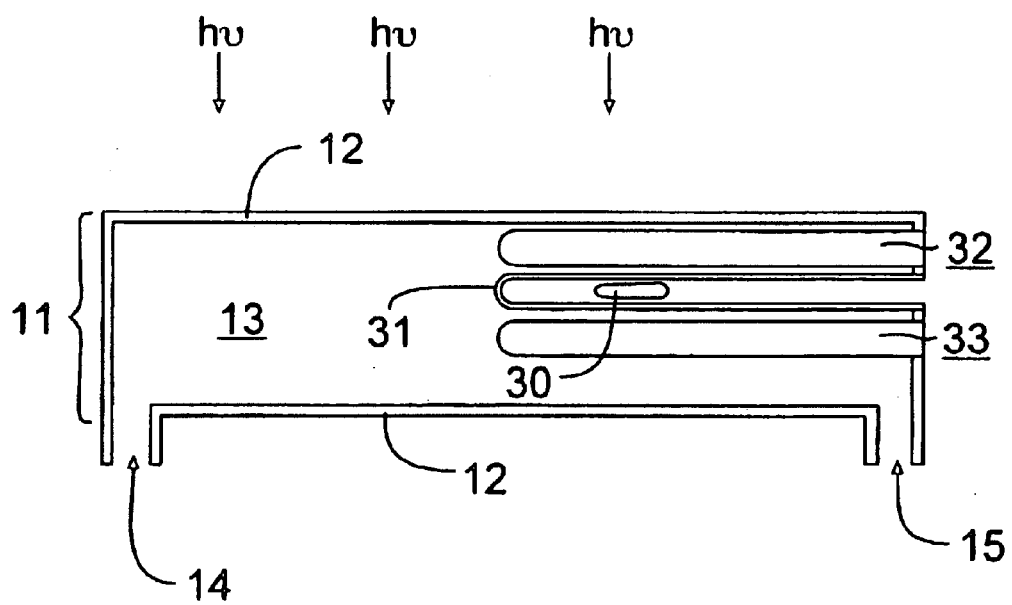
FIG. 2 is a cross-sectional view of a device 10 for measuring the organic content of a photo-oxidized sample liquid according to another embodiment of the present invention.

Both FIGS. 1 and 2 provide schematic representational illustrations. The relative locations, shapes, and sizes of objects have been exaggerated to facilitate discussion and presentation herein.

DETAILED DESCRIPTION

The present invention provides a device useful in the photo-oxidation of a sample liquid and in the measurement of the oxidized carbon content thereof. Fundamentally, the device comprises a cell, at least two elongate probes, and a temperature sensitive element.

The cell—into which is loaded the sample liquid to be subjected to photo-oxidized carbon content analysis—comprises a rigid outer wall that encloses a continuous predetermined internal volume (i.e., the cell's "intracelluiar" volume). To permit photo-oxidation of the loaded sample liquid, the rigid enclosing wall must be light-transmissive. In particular, the rigid outer wall must be sufficiently light-transmissive to allow the passage therethrough of photo-irradiation or an intensity sufficient for effecting the photo-oxidation of the loaded sample.

The elongate probes—which provides collectively the ability to measure temperature and conductivity—are structured and incorporated into the device penetrating through the rigid outer wall and extending substantially into the cell's internal volume. It is an important feature of the present invention that at least one of the elongate probes be hollow at least partially along its length, preferably within a region that is substantially deep within cell's "intracellular" volume, and even more preferably, the center thereof. A typical hollow configuration would be a central coaxial bore running most of the length of the elongate probe.

The temperature sensitive element—which provides the temperature-dependent electrical signal used for measuring temperature—is positioned inside the hollow elongate probe, preferably in the aforementioned region deep within the cell's "intracellular" volume, to allow the taking of temperature readings within that area.

There is no particular limitation to the exact location of the temperature sensitive element within the cell's intracellular volume, nor is there any particular limitation to the number of or specific functional assignation for each of the elongate probes. Thus, it will be appreciated that the present invention is subject to broad variation. Regardless, two principal illustrative embodiments stand out as particularly well-suited to accomplishing certain of the aforementioned objectives. While they differ in other respects, these two embodiments—illustrated schematically in FIGS. 1 and 2—are differentiated first and foremost on the functional configuration of the hollow elongate probe into which the temperature sensitive element is deposited.

As shown in FIG. 1, a device according to a first embodiment of the present invention comprises a cell 11, a plurality of elongate probes 16 and 17, and a temperature sensitive element (i.e., thermistor 19). More particularly, the device 10 is formed of a cell 11 having a rigid light-transmissive wall 12 enclosing a continuous predetermined internal volume 13 (i.e., the "intracellular" volume). An inlet 14 and an outlet 15 is located in the rigid light-transmissive wall 12 of the cell 11, providing a conduit for liquid to be loaded into and removed from the intracellular volume 13. As shown, the inlet 14 is spaced from the outlet 15 along a portion of the cell 11, joining the cell 11 substantially orthogonally to its longer axis. While a substantially orthogonal arrangement is preferred in respect of certain fluid dynamics and control parameters sought in the development of this embodiment, other arrangements—such as a "straight through" flow design—may be used.

As shown in FIG. 1, two elongate electrode probes 16 and 17 extend into the interior volume 13 of the cell 11 and are sealed liquid tightly at their entrance to the interior volume 13 at the cell wall 12. The elongate electrode probes 16 are 17 are arranged substantially parallel to each other spaced apart. Preferably, they are spaced apart by a relatively small distance. One of the elongate electrode probes—in this case elongate electrode probe 16—is hollow and contains within its bore 18 the temperature sensitive element 19—Electrical potential is supplied to the elongate electrode probes by leads 20 and 21. Electrical potential is supplied to the temperature sensitive element 19—preferably from a separate power supply—by lead 22.

Preferably, the distance between the elongate electrode probes 16 and 17 is about 0.01 inch (0.0254 cm) to about 0.1 inch (0.254 cm). The cell 11 should have a cell constant as low as practicable, whereby sensitivity in the measurement of conductivity is optimized. Preferably, the cell constant should be between about 0.05 cm$^{-1}$ and about 1 cm$^{-1}$.

In the second embodiment, as shown in FIG. 2, a temperature sensitive element 30 (e.g., a thermistor) is mounted in a separate stand-alone hollow elongate probe 31, rather than within one of the two elongate electrodes probes 32 and 33 used to measure the conductivity of sample liquid. In the second embodiment, the hollow elongate probe 31 is positioned between the two elongate electrode probes 32 and 33, preferably in a plane offset from the plane defined by electrode proves 32 and 33 so as to not interfere inordinately with their ability to obtain an accurate measurement of conductivity. In other embodiments (not shown), the probe 31 may be positioned "in line" and directly between the two electrode probes 32 and 33, for example, when does so does not interfere with their conductivity measurements.

When employing a third, dedicated thermal probe, there is no fundamental critical limitation to the positioning of such probe relative to the paired electrode probes. The third thermal probe may be parallel or orthogonal to the electrode probes, or other intermediate angular arrangements.

Preferably, the hollow elongate probe 31 of the second embodiment is made of a thermally conductive material and has as low thermal mass (e.g., a thermal mass lower than that possessed by the elongate electrode probes 32 and 33). Hollow elongate probe 31 may also be made of electrically conductive materials, provided it is electrically isolated or insulated from the elongate electrode probes 32 and 33. And in this regard, it can be made of the same material as the electrodes 32 and 33.

In both the first and second embodiments of the present invention, the elongate probes (16, 17, 30, 31, and 32) are preferably rod shaped (i.e., long, straight, and thin), through other configurations can be utilized (e.g., long, planar probes). Furthermore, although the probes are illustrated in FIGS. 1 and 2 penetrating the depths of cell 11 only partially, other preferred embodiment would include elongate probes that completely traverses the length of cell 11 though its intracellular volume 13, such as disclosed in, for example, U.S. Pat. No. 5,677,190, issued to P. C. Melanson et al. on Oct. 14, 1997.

The closed end of a hollow elongate probe may be made during formation, such as by molding or by drawing of the material from which it is made in that shape. Alternatively, one can simply crimp the end or otherwise seal it, such as by a resin (e.g., epoxy), molten plastic, or metal, which is then cooled into a solid form, a cap, or a compression fitting, so as to form a liquid tight seal at the end of the hollow elongate probe which extends into the liquid. This is of course unnecessary where the hollow elongate probe traverse the entire length of the cell 11. Metal and other materials having very little or no extractable organic or inorganic content are preferred for the embodiments represented by FIGS. 1 and 2. While circular tubes are preferred in respect of their ready manufacture, other cross-sectional shapes may be used, such as squares, rectangles, and like polygons.

The elongate probes (hollow or otherwise) are preferably made of a material that is both electrically and thermally conductive. Materials that have both characteristics include, but are not limited to, carbon or graphite based composites; thermally conductive plastics (such as the inherently thermally conductive polyanaline resins); a metal, carbon and/or graphite filled thermoplastic or epoxy; certain ceramics; and metal. Metal and ceramics are highly preferred.

Preferred metals include but are not limited to stainless steel, copper, aluminum, nickel, chromium, tungsten, titanium, palladium, silver, gold and various alloys. Preferably, the metals selected are inert in the liquid, do not appreciably oxidize, and are quick to reach equilibrium temperature within the sample liquid. Such metals include stainless steel, tungsten, titanium, palladium, silver, and gold. In respect of material costs, stainless steel, tungsten, titanium and palladium are preferred.

It is generally preferred that at the least the hollow elongate probe containing the temperature sensitive element—but preferably all electrodes used in the device—have a low thermal mass. Preferably, it should have as low a thermal mass as possible in consideration of its size and—if also functioning as an electrode—its electroconductive capacity. In this way, the temperature sensitive element will measure more closely the actual sample liquid temperature, with minimized effect thereon by the materials used to form the hollow elongate probes.

The volume of cell 11 will be effected by the length and shape of the device's elongate probes. Typically, the cell of the present invention has a cell volume of between about 0.05 milliliters and about 2.0 milliliters, with a volume of about 0.6 to 0.5 milliliters being preferred.

In respect of the construction of cell 11, principal consideration in the selection of materials and their assemblage is heavily weighted toward that which advanced most efficiently and reliably the containment of a predetermined volume of sample liquid within the cell 11 and in the photo-oxidation thereof. Hence, in respect of the construction of cell wall 12, rigidity (advancing reliable containment) and light-transmissivity (advancing reliable photo-oxidation) are quite important. Low organic and inorganic extractable content is also quite important.

Good rigidity and light-transmissivity are accomplished where the cell wall is essentially tubular in shape having at least a window formed of a solid material that is transparent to radiation of interest. Glass, ceramic, plastic or metal with glass and plastics are desirable due to their low- to non-electrical conductivity, their relatively low thermal mass and heat loss, and their inertness to liquids most likely sought to be tested. Where the device is to be used for the oxidation of organics in water to carbon dioxide, the cell "tube" is formed of a synthetic fused silica or fused quartz material transmissive of 185 and 254 nm ultraviolet wavelengths. In one construction, a "Supracil" fused quartz tube is provided having a 5.0 millimeter inside diameter, a 7.0 millimeter outside diameter, and a 0.75 inch length (1.905 centimeter).

Although the practice of the present invention envisions and would allow the use of "windowed" cells (i.e., a cell that is opaque but for provision therein of a light-admitting window), in respect of simplicity of manufacture, a cell that is made completely of one continuous rigid light-transmissive material is preferred.

To accomplish photo-oxidation of organics in a sample liquid, a photo-irradiation source (not shown) is utilized. Where the device is to be utilized for the oxidation of organics in water to carbon dioxide, the photo-irradiation source is one capable of emitting radiation in the 185 and 254 nm ultraviolet wavelengths. A typical low pressure mercury vapor lamp ultraviolet radiation in the 184 and 254 nm wavelength ranges is quite efficient in the destruction of organics (more specifically, emitting effective amounts of radiation at 184.9 nm and 253.6 nm). The intensity of the source will vary, of course, among different applications. However, it will be appreciated that shorter photo-reaction times can be accomplished with more intense radiation sources, though shielding of the more UV sensitive cell components may be warranted if such intense sources are to be used.

The positional relationship of a lamp (not shown) providing ultraviolet irradiation to the interior volume 13 of cell 11 is also subject to variation, depending on particular objectives that do not limit the scope of the present invention, and are well within the skill in the art. Regardless, it is desirable to space the lamp from the cell by a distance approximately equal to the diameter of the enclosed internal volume 13 of the cell 11, such that radiation from the lamp will tend to be concentrated more uniformly throughout the internal volume, thus reducing the severity of thermal gradients. Additional focussing means could also be provided, but may add to the expense of the cell. If further improvement in reaction time is desired, it will be appreciated that many reactions (including the oxidation of organics in water) can be accelerated by application of DC power. This can be accomplished, for example, by running DC current from a power source between the device's elongate electrode probes.

In one representative arrangement, the ultraviolet lamp (e.g., UV lamp Model 71-9025-01, available from BHK Corporation, Pomona, Calif.) is disposed approximately 5 mm from the rigid light-transmissive wall 12 of cell 11, cell 11 having a 7 mm OD. Other radiation sources may require differing arrangements to ensure the efficient and controllable conduct of photo-oxidation reactions in the internal volume 13.

The temperature sensitive element used for the present invention must be capable of providing a temperature-dependent electrical signal and must be small and compact enough to be placed within the bore of a hollow elongate probe, but is in all other respects quite variable in construction. While there are several known electrical components that possess the mandatory characteristics, the preferred temperature sensitive element is a thermistor, such as 30 k thermistor (US Sensor part number PS303J2) available from US Sensor of Orange, Calif.

The temperature sensitive element can be fixed within the hollow elongate probe by bonding with, for example, a thermally conductive epoxy material. Other adhesives and potting compositions can, of course, be employed. Mechanical anchors (e.g., tabs, indents, interlocking grooves, friction fittings, ledges, etc.) formed in the temperature sensitive element and/or the probe's inside wall are also contemplated.

As an alternative to the use of a thermistor, one can also use a so-called "resistive thermal device" (RTD) as a temperature sensitive element. Like thermistors, RTDs are generally small electrical components that measure temperature based on changes in their resistance in response thereto. Thermocouples—which employ a combination of dissimilar metals to provide electrically-measurable temperature-dependent resistance characteristics—are also useful.

It is desirable to fit the temperature sensitive element snugly against the inside diameter of hollow elongate probe, thereby improving its accuracy in measuring the temperature of sample liquid. In this regard, the ability to use and/or design compact temperature sensitive elements—e.g., "thin film"-type temperature sensitive elements—would allow further reduction of the required diameter needed for snugly housing the temperature sensitive element within the hollow elongate probe. This can be quite important considering that under currently available technology, the manufacture of a thin wall tube having a wall thickness in the order of about 0.002 inch (0.00508 cm) or lower is difficult, thereby constraining the potential outside diameter of the hollow elongate probe.

In addition to the use of temperature sensitive element within the bore of hollow elongate probe, another consideration important to the construction of the inventive device is accomplishment of a comparatively low "cell constant".

As mentioned above, the "cell constant" is defined as the value of the distance between the electrodes (in cm) divided by the electrode surface area (in cm$^2$), yielding a constant value in units of cm$^{-1}$.

One method of approximating the cell constant (K)—i.e., for obtaining an upper-bound estimate therefor—is to calculate the effective electrode surface area. The "effective" area is about half the total surface area of the electrode, since only one half of the electrode faces the other electrode, and hence, the expression: $\frac{1}{2}(\pi DL)$, wherein "D" and "L" are the diameter and length of the electrode respectively. This value is multiplied by the distance between the electrodes, and hence, the expression: $K = d/(\frac{1}{2}(\pi DL))$, wherein "d" is the distance between the electrodes.

The cell constant can also be empirically determined by measuring the conductivity of a salt solution (e.g., NaCl or KCl) which has a known conductance value (e.g., a 1 millimolar concentration of KCl has a conductivity of 147 microSiemens/cm at 25° C.) and using that value to calculate the cell constant from the reported microSiemens value.

A small cell constant is particularly desirable when the conductivity to be measured is very small, such as in high purity water and aqueous solutions. In this regard, it will be appreciated that conductivity is measured by applying a voltage to cell electrodes and measuring the resulting current. When conductivity is low, resistance is high and current is low. Under such circumstance, a small cell constant is desirable because the smaller the cell constant, the greater the surface area to distance ratio and the greater the signal (measured current) from the cell. This results in a more accurate measurement.

One can strike a desirable balance between thermal mass and cell constant, by setting the distance (d) between the probes responsible for measuring conductivity to the smallest value practical to reduce the cell constant (K) to its lowest possible value.

Another factor in determining the cell constant of a device according to the present invention is the outside diameter of the temperature sensitive element, which presumptively defines also the minimal inside diameter of the hollow elongate probe which houses it. In a preferred embodiment, the inside diameter of the hollow elongate probe containing the temperature sensitive element is from about 0.008 inch to about 0.090 inch (0.0203 cm to about 0.203 cm), and preferably, from about 0.012 about 0.02 inch (0.0254 cm to about 0.0508 cm). The outside diameter (D) of the probes should be from about 0.01 inch to about 0.1 inch (0.0254 cm to about 0.254 cm), and preferably, from about 0.02 inch to about 0.03 inch (0.0508 cm to about 0.0762 cm). The effective length (L) of the probes is typically from about 0.25 inch to about 2.0 inch (0.635 cm to about 5.08 cm), preferably from about 0.5 inch to about 1.0 inch (1.27 cm to about 2.54 cm). (The effective length is a factor in the cell constant and reflects the length of the electrode within the cell body. As a practical matter, the actual length will typically be longer than the effective length in order to install the probe into the cell housing and make the electrical connections to them as required). Using the formula $K=d/(\frac{1}{2}(\pi DL))$, a cell constructed within the ranges of this embodiment, having two electrodes of 0.025 inch (0.0635 cm) outside diameter, an inside diameter of 0.017 inch (0.0432 cm), spaced apart 0.0248 inch (0.063 cm), and an effective length of 0.75 inch (1.905 cm) will have a desirable cell constant of 0.33 $cm^{-1}$.

Because the cell's internal volume is effected (i.e., diminished) by the physical dimensions of its contained electrode probes, it will be appreciated that there is a trade-off between the cell constant and the cell volume. This should be considered in the construction of cells used for the present invention.

In addition to its product embodiments, the present invention also provides a related method for measuring the total oxidizable carbon content of a liquid employing variants of said embodiments.

In view of its sensitivity (i.e., within ppb range), the method is particularly suited for analysis of so-called "ultra-pure" liquids (e.g., reagent-grade water). Performing the method on low-purity liquids may yield less meaningful results. In performing water TOC analysis using the method, it is highly desirable that the water under analysis be pre-filtered, purified, and/or otherwise pre-treated to obtain a resistivity of approximately greater than 1 mega-ohms-cm, and preferable greater than 10 mega-ohm-cm.

The method commences with the provision of a device comprising a cell, at least two elongate probes, and a temperature sensitive element. The device of the methodology is drawn along the many similar lines as the product embodiments. Thus, the cell comprises features reminiscent of the product embodiments: i.e., a rigid light-transmissive outer wall enclosing a continuous predetermined internal volume; at least two elongate probes penetrate through said rigid outer wall and extend substantially into said internal volume; the probes are collectively capable of measuring the temperature and the conductivity of said sample liquid; at least one of the elongate probes is hollow at least partially along its length; and the temperature sensitive element is capable of providing a temperature-dependent electrical signal and is positioned inside one of said hollow elongate probes.

Provided with a suitable device, an initial sample of the liquid under analysis—which is used to obtain a baseline conductivity value—is loaded into device's internal volume. The temperature and conductivity of the initial sample are measured intracellularly by the device's probes. A thermally-corrected conductivity value for the initial sample is then calculated using the measured temperature and measured conductivity values.

An industry-accepted formula for obtaining a thermally-corrected conductivity value DC is $DC=DM/(1+A(TM-TC))$, wherein "DM" is the measured conductivity value, "A" (alpha) is the published temperature correction factor characteristic of the sample liquid (e.g., for pure water, alpha is 0.02), "TM" is the measured temperature value, and "TC" is 25° C. This formula is generally applicable under room temperature conditions, plus or minus 20° C. Other formulae—well-known to those skilled in the art—are widely available.

After the conductivity and temperature readings are taken from the initial sample liquid, the sample can either be retained within the internal or replaces with a second sample. Retention is preferred. Regardless, where a second sample is to be loaded, this is accomplished, for example, in devices 10 provided with an inlet 14 and an outlet 15, by opening said outlet and inlet (e.g., by opening valves and like mechanisms combined therewith), and flushing out the first sample with the second sample, preceded (or not) with a volume of the same (or other) liquid to "clean" the device's internal volume.

Regardless of whether the initial sample is retained or replaced with a second sample, the loaded sample is photo-oxidized. More particularly, the loaded sample is exposed to photo-irradiation (preferably, in the ultraviolet wavelengths) through the device's rigid light-transmissive outer wall at an intensity and duration sufficient to effect at least partial photo-oxidation of any carbon species contained in said second sample.

At the conclusion of photo-irradiation, both the temperature and conductivity of the loaded sample are measured intracellularly by the device's probes. A thermally-corrected conductivity value for the photo-oxidized sample is then calculated using the measured temperature value and the measured conductivity value utilizing, for example, the same formula set forth above.

Finally, the total oxidizable carbon content of said liquid is calculated using the pre- and post-photo-oxidation thermally-corrected conductivity values. The total oxidizable content can thereafter be derived from the difference between the two values by calculations known to those skilled in the art.

EXAMPLE

A device according to the present invention was compared with two commercially available cells: i.e., an "A1000" cell (available from the Anatel Corporation of Boulder, Colo.) and an "Access 643" cell (a so-called "button cell" available from Anatel Corporation). The inventive device was manufactured to have a cell constant of 0.30 $cm^{-1}$ The A1000 cell had a cell constant of 0.05 $cm^{-1}$. The Access 643 cell had a cell constant of 0.50 $cm^{-1}$.

The inventive device used a 30K thermistor located intracellularly within the bore of one of two parallel elongate electrode probes. The "Access 643" button cell had a 30K thermistor potted extracellularly in one of its electrode. The "A1000" cell had a 30K thermistor potted extracellularly to the surface of one of its electrodes.

The inventive device and each comparison cell were loaded with static sample liquids and subjected to a "salt thermometer test", i.e., they were assessed utilizing salt solutions of known conductivity under varying known temperatures. The salt thermometer tests sought to determine the difference between the actual water temperature (i.e., the temperature corresponding to the known conductivity of the salt solution) and the measured water temperature (i.e., as measured by the temperature sensor within each cell). Photo-oxidation was conducted continuously utilizing the cell's ultraviolet irradiation source.

The measured and actual temperatures for each cell and for the inventive device were recorded. NaCl was used for the salt thermometer test since the relationship between temperature and conductivity for varying NaCl salt solutions are well established and widely documented.

The data collected from each study is presented in following Tables 1 to 3. All temperatures reported are in centigrade.

TABLE 1

Salt-Thermometer Test Results for Inventive
Device ("Intracellular Temperature Measurement")

| Measured Temp | Salt Therm. Temp | Difference | % Difference |
| --- | --- | --- | --- |
| 17.30 | 17.31 | 0.01 | 0.08 |
| 24.91 | 24.77 | −0.14 | −0.56 |
| 33.22 | 32.98 | −0.24 | −0.72 |
| 41.49 | 41.16 | −0.34 | −0.82 |
| 49.59 | 49.48 | −0.11 | −0.21 |
| 53.78 | 53.84 | 0.07 | 0.12 |
| 58.12 | 58.32 | 0.20 | 0.34 |

TABLE 2

Salt-Thermometer Test Results for "Acess 643"
Button Cell ("Extracellular Temperature Measurement")

| Measured Temp | Salt Therm. Temp | Difference | % Difference |
| --- | --- | --- | --- |
| 20.87 | 19.10 | −1.77 | −9.29 |
| 26.64 | 25.27 | −1.38 | −5.46 |
| 33.64 | 32.45 | −1.20 | −3.69 |
| 40.82 | 39.76 | 1.06 | −2.65 |
| 47.52 | 47.01 | −0.51 | −1.08 |
| 51.26 | 51.01 | −0.25 | −0.49 |
| 55.08 | 55.14 | 0.06 | 0.12 |

TABLE 3

Salt–Thermometer Test Results for "A1000"
Cell ("Extracellular Temperature Measurement")

| Measured Temp | Salt Therm. Temp | Difference | % Difference |
| --- | --- | --- | --- |
| 16.79 | 17.29 | 0.50 | 2.91 |
| 25.31 | 25.67 | 0.36 | 1.40 |
| 34.26 | 34.60 | 0.34 | 0.99 |
| 43.30 | 43.66 | 0.36 | 0.82 |
| 52.29 | 52.92 | 0.63 | 1.19 |
| 56.77 | 57.59 | 0.82 | 1.42 |
| 61.63 | 62.64 | 1.02 | 1.62 |

It can be observed from Tables 1 to 3 that the inventive device yields measured temperature values closer to the actual temperature values than provided by the commercial products. Typically, the probe has a thermal reading within +/−1.0% of that measured by a salt thermometer test, preferably less than +/−0.75% based on that test over a wide range of temperatures. The accuracy of the inventive device was desirably well within 1° C. of the value measured by the salt thermometer test—and even more desirably, within 0.5° C.—over a wide range of temperatures above and below 25° C. We are unaware of any precedent for such accomplishment in any other photo-oxidation-based conductivity-measuring device.

While the present invention has been described with reference to certain particular embodiments thereof, those skilled in the art, having the benefit of the teachings of the present invention set forth herein, can effect numerous modifications thereto. These modifications are to be considered as being encompassed within the scope of the present invention as set forth in the appended claims.

What is claimed is:

1. A device useful in the photo-oxidation of a sample liquid and in the measurement of the oxidized carbon content thereof, the device comprising:

a cell comprising a rigid light-transmissive outer wall enclosing a continuous predetermined internal volume, the transmissivity of the rigid outer wall being sufficient to allow the passage therethrough of photo-irradiation of an intensity sufficient for effecting said photo-oxidation of said sample liquid when said sample liquid is loaded into said continuous predetermined internal volume;

at least two elongate probes penetrating through said rigid outer wail and extending substantially into said continuous predetermined internal volume, the probes collectively capable of measuring the temperature and the conductivity of said sample liquid, at least one of the elongate probes being hollow at least partially along its length; and a temperature sensitive element, capable of providing a temperature-dependent electrical signal, positioned inside one of said hollow elongate probes.

2. The device of claim 1, wherein the device comprises a total of two of said elongate probes, the elongate probes configured as paired electrodes that function together for said measurement of said conductivity.

3. The device of claim 1, wherein the device comprises:

a pair of said elongate probes configured as paired electrodes that function together for said measurement of said conductivity; and a third elongate probe positioned substantially between said pair of said elongate probes, the third elongate probe being hollow at least partially along its length, said temperature sensitive element being positioned inside said third elongate probe.

4. The device of claim 1, wherein said cell further comprises an inlet and an outlet, said inlet configured for loading sample liquid into said continuous predetermined internal volume, said outlet configured for removing sample liquid loaded into said continuous predetermined internal volume.

5. The device of claim 1, wherein said rigid outer wall is at least partially made of fused quartz.

6. A method for measuring the total oxidizable carbon content of a liquid, the method including the steps of:

a) providing a device comprising a cell, at least two elongate probes, and a temperature sensitive element, wherein said cell comprises a rigid light-transmissive outer wall enclosing a continuous predetermined internal volume, wherein said at least two elongate probes penetrate through said rigid outer wall and extend substantially into said internal volume, the probes collectively capable of measuring the temperature and the conductivity of said sample liquid, at least one of the elongate probes being hollow at least partially along its length, and wherein said temperature sensitive element is capable of providing a temperature-dependent electrical signal and is positioned inside one of said hollow elongate probes;

b) loading a sample of said liquid into said internal volume, measuring the temperature and conductivity of said sample, then calculating a first thermally-corrected conductivity value for said sample using its measured temperature and its measured conductivity;

c) exposing either said sample or a second sample of said liquid loaded into said internal volume to photo-irradiation through said rigid light-transmissive outer wall at an intensity and duration sufficient to effect at least partial photo-oxidation of any carbon species contained in the loaded sample, measuring the temperature and conductivity of said loaded sample at the conclusion of said exposure, then calculating a second thermally-corrected conductivity value for said loaded sample using its measured temperature and its measured conductivity; and d) calculating the total oxidizable carbon content of said liquid using said first and second thermally-corrected conductivity values.

7. The method of claim 6, wherein the device comprises:

a pair of said elongate probes configured as paired electrodes that function together for said measurement of said conductivity; and a third probe positioned in said internal volume substantially between said pair of said elongate probes, the third probe being hollow at least partially along its length, said temperature sensitive element being positioned inside said third probe.

8. The method of claim 6, wherein the device comprises:

a total of two of said elongate probes, the probes configured as paired electrodes that function together for said measurement of said conductivity.

9. The method of claim 6, wherein the photo-irradiation in step (c) is ultraviolet photo-irradiation.

10. The method of claim 6, wherein said liquid is water.

* * * * *